United States Patent
Ogawa et al.

(10) Patent No.: US 6,339,146 B1
(45) Date of Patent: *Jan. 15, 2002

(54) CYCLOALKYLATED BETA-GLUCOSIDE

(75) Inventors: Koichi Ogawa; Masayasu Takada, both of Fuji (JP)

(73) Assignee: Nikon Shokuhin Kako Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,714

(22) Filed: Jul. 29, 1999

(30) Foreign Application Priority Data

Jan. 13, 1999 (JP) .......................................... 11-006027

(51) Int. Cl.$^7$ ................................................ C07H 15/20
(52) U.S. Cl. ...................................... 536/4.1; 536/18.6
(58) Field of Search ................................. 536/4.1, 18.6

(56) References Cited

FOREIGN PATENT DOCUMENTS

| JP | 48-32846 | 5/1973 |
|----|----------|--------|
| JP | 63-25859 | 2/1988 |
| JP | 63-258591 | 10/1988 |
| JP | 6-336401 | 12/1994 |
| JP | 10-33647 | 2/1998 |

OTHER PUBLICATIONS

Andersen et al. "Natural cyclopentanoid cyanohydrin glycosides. Part 17. Cyanogenesis of Passiflora foetida." Phytochemistry, 47(6): 1049–1050, 1998.*
Furumoto et al. "Enzymic synthesis of glucoside derivatives of validamine and valienamine", Chem. Pharm. Bull., 40(7): 1871–1875, 1992.*
T. Niwa et al., Agric. Biol. Chem. 34, 966–968 (1970).
G. Legler et al., Carbohydr. Res., 128, 61–72 (1984).
U. Fuhrmann et al., Biochem. Biophys. Acta., 825, 95–1109 (1985).
A. Welter et al., Phytochem. 15, 747–749 (1976).
S. Ogawa et al., J. Chem. Soc. Chem. Commun., 1843–1844 (1987).
R.A. Farr et al., Tetrahedrom Lett., 31, 7109–7112 (1990).
G. Papandreou et al., J. Am. Chem. Soc. 115, 11682–11690 (1993).
J. Lehmann et al. Leibigs Ann. Chem., 805–809 (1994).
English abstract of JP 6–336401 A.
English abstract of JP 10–33647 A.
I.E. Ackermann et al., J. Plant Physiol., 134, 567–572 (1989).
K. Sakata, Oyo Tositsu Kagaku [Applied Saccharide Science], vol. 45, No. 2, 123–129 (1998).
English abstract of JP 48–32846 A.
Miyakoshi et al., Yu Kagaku (Oil Science), vol. 43, No. 1, 31–38, (1994).

* cited by examiner

Primary Examiner—Gary Geist
Assistant Examiner—Devesh Khare
(74) Attorney, Agent, or Firm—Burnes, Doane, Swecker and Mathis

(57) ABSTRACT

There are disclosed a compound represented by the following general formula I wherein R represents a cyclic hydrocarbon group, and n represents 0 (zero) or an integer not less than 1, as well as β-glucosidase inhibitor, aromatic substance formation inhibitor, plant life lengthening agent, each of which contains at least one of compound represented by the aforementioned general formula I as an active ingredient, and plant or a part thereof in which formation of aromatic substance is inhibited by the aforementioned aromatic substance formation inhibitor. The present invention provides a novel compound that has β-glucosidase inhibition activity and can easily be produced in an industrial process, as well as a β-glucosidase inhibitor and aromatic substance formation inhibitor each containing such a novel compound as an active ingredient, and plant or part thereof in which the formation of aromatic substances is inhibited by the aforementioned aromatic substance formation inhibitor.

5 Claims, No Drawings

CYCLOALKYLATED BETA-GLUCOSIDE

BACKGROUND OF THE INVENTION

1. Field of the Invention

The present invention relates to a cycloalkyl β-glucoside, a β-glucosidase inhibitor, an aromatic substance formation inhibitor that inhibits the formation of plant aromatic substance, and a plant or a part thereof in which the formation of aromatic substances is inhibited by the aforementioned aromatic substance formation inhibitor, as well as a plant life lengthening agent.

2. Description of Related Art

As inhibitors for enzymes which hydorolyzed glycosidic linkages such as glucosidase, various substances including saccharides and proteins derived from plants and microorganisms, synthetic oligosaccharide derivatives and the like have hitherto been reported. Among those, as for inhibitors of β-glucosidase, many substances derived from microorganisms or plants and obtained by organic synthesis have been described. Examples of such substances include, as for those derived from microorganisms or plants, nojirimycin (T. Niwa et. al., Agric. Biol. Chem. 34. 966 (1970)), 1-deoxynojirimycin (G. Legler et. al., Carbohydr. Res., 128, 61 (1984)), castanospermine (U. Fuhrann et. al., Biochem. Biophys. Acta., 825, 95 (1985)), 2,5-dihydroxymethyl-3,4-dihydroxypyrrolidine (A. Welter et. al., Phytochem. 15, 747 (1976), validamine (S. Ogawa et. al., J. Chem. Soc. Chem. Commun., 1843 (1987) and the like, and as for those obtained by organic synthesis, aminocyclopentane polyol (R. A. Farr et. al., Tetrahedron Lett., 31, 7109 (1990), cyclic amidine (G. Papandreou et. al., J. Am. Chem. Soc. 115, 11682 (1993), cyclic guanidine (J. Lehmann et. al. Leiebigs Ann. Chem., 805 (1994), and the like. These inhibitors are analogues of the substrates for glucosidases containing a nitrogen atom without exception.

These inhibitors, are useful physiological active substances which can be used for various biochemical researches as an enzyme reaction analysis reagent, an affinity carrier, a agent for analysis of function and recognition mechanism of glycoprotein and the like, and it has also been attempted to utilize them as medical or agricultural chemicals in these days. These inhibitors which are expected to be applicable in various fields, as mentioned above, have been conventionally been produced by extraction from microorganisms or plants, or by organic synthesis.

However, in the case of those substances derived from microorganisms, it is quite difficult to purify such inhibitors from microbial culture broth. As for those ones derived from plants, their present amount is very little in the first place, and hence it is difficult to extract and purify them from plants. Thus, the both methods involve many problems as a method for industrial production. For example, they suffer from limitations concerning with cost, yield and the like. Further, most of reported conventional β-glucosidase inhibitors are their substrate analogues containing a nitrogen and therefore it is not easy to produce them through enzymatic synthesis or organic synthesis. That is, in the case of organic synthesis, only for introducing a nitrogen atom into a saccharide structure, several steps of organic synthesis reaction are required to perform, and hence it is disadvantageous as an industrial process. For the aforementioned reasons, it has hitherto been difficult to industrially produce glucosidase inhibitors which is utilizable for biochemical applications. Therefore, there has been desired an inhibitor having a relatively simple structure of which industrial production is possible.

By the way, a method for changing plant fragrance has been known, which comprises allowing a plant to absorb an aromatic substance, β-glucoside (Japanese Patent Unexamined Publication [KOKAI] No. 6-336401). This method consists, of adding aroma to a plant. Therefore, it was insufficient for improving aroma of plant with an unpleasant smell. Further, there has also been known changing plant fragrance by adding a dihydric alcohol such as propylene glycol as plant fragrance deodorizing agent (Japanese Patent Unexamined Publication [KOKAI] No. 10-33647). Although this patent document describes that unpleasant smell of plant could be deodorized by adding a dihydric alcohol, its effectiveness was not satisfactory one. Further, while it is of course required to reduce fragrance of plants generally considered to be unpleasant, for example, that of gypsophila, lily, chrysanthemum etc., it may be also desirable as the case may be to reduce fragrance of plants considered pleasant, for example, that of rose, jasmine, lavender and the like. Therefore, it has been desired to develop an aromatic substance formation inhibitor that acts on any kind of aroma.

Currently, as plant aromatic substances, there are known, for example, monoterpene alcohols such as geraniol and citronel, aromatic alcohols such as phenethyl alcohol and benzyl alcohol and the like. These alcohols are contained in various flowers, teas, fruits, wines and the like, and it has become clear that they also exist as glycosides in addition to their free forms. Further, there have also been reported that the aromatic substance precursors of the aromatic substances such as geraniol and phenethyl alcohol, which are major aromatic substances of rose and the like, are β-glucosides, and biosynthesized in leaves and petals, respectively, and that β-glucosidases play an important role in the production process of aromatic substances (I. E. Ackermann et. al., J. Plant Physiol., 134, 567-572 (1989); K. Sakata, Oyo Tositsu Kagaku [Applied Saccharide Science], Vol.45, No.2, 123–129 (1998)).

That is, plant fragrance is formed by a mechanism that the aromatic substance precursor, β-glucoside, is hydrolyzed by β-glucosidase to liberate an aromatic substance. If the function of β-glucosidase in this mechanism can be inhibited, the aromatic substance precursor, β-glucoside, would not be hydrolyaed, and hence an aromatic substance will not be formed or its formation will be reduced. That is, it can be considered that, if β-glucosidase can be inhibited, the aromatic substance to be liberated is reduced and smell can be reduced.

SUMMARY OF THE INVENTION

Therefore, an object of the present invention is to provide a novel compound that has β-glucosidase inhibition activity and can easily be produced in an industrial process. Furthermore, another object of the present invention is to provide an aromatic substance formation inhibitor containing such a novel compound as an active ingredient, and plant or part thereof in which the formation of aromatic substances is inhibited by the aforementioned aromatic substance formation inhibitor.

As a result of the present inventors' researches, it was found that cycloalkyl β-glucosides which can be easily produced by organic synthesis or enzymatic synthesis had the β-glucosidase inhibition activity. Because these β-glucosides do not contain a nitrogen atom, their synthesis does not require any complicated synthetic process for introducing a nitrogen atom, and hence they can be produced by a relatively simple synthetic process, which means that their industrial production is possible. Furthermore, the present inventors studied various candidate aromatic substance formation inhibitors for plants from the viewpoint of searching substances capable of inhibiting β-glucosidase to prevent the hydrolysis of β-glucoside, thereby inhibiting the formation of aromatic substances, to find aromatic substance formation inhibitors for plants that have suitable activity for alleviating unpleasant smell and strong aroma of plants. As a result, it was unexpectedly found that the aforementioned cycloalkyl β-glucosides had marked activity for inhibiting the formation of plant aromatic substances and consequently reducing the amount of aromatic substances released from plants, and further found that they did not producing phytotoxicity against plants and also had life lengthening effect. Thus, they accomplished the present invention.

Cycloalkyl β-glucoside

The present invention relates to compounds represented by the following general formula (I).

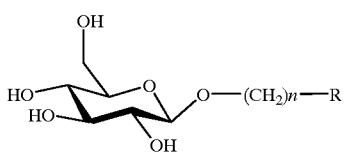

(I)

In the formula, R represents a cyclic hydrocarbon group, and n represents 0 (zero) or an integer not less than 1.

The present invention also relates to a β-glucosidase inhibitor which contains at least one of compound represented by the aforementioned general formula I as an active ingredient; an aromatic substance formation inhibitor which contains at least one of compound represented by the aforementioned general formula I as an active ingredient; a plant or a part thereof in which formation of aromatic substance is inhibited by the aforementioned aromatic substance formation inhibitor; and a plant life lengthening agent which contains at least one of compound represented by the aforementioned general formula I as an active ingredient.

PREFERRED EMBODIMENTS OF THE INVENTION

Cycloalkyl β-glucoside

In the general formula (I), n is 0 (zero) or an integer not less than 1, and does not have any particular upper limit. However, considering ease of production, for example, if a raw material is commercially available or not, n is preferably 3 or less. Of course, it is not intended to exclude those compounds where n is 4 or more.

In the general formula (I), R represents a cyclic hydrocarbon group, and specific examples thereof include a cyclopropyl group, a cyclobutyl group, a cyclopentyl group, a cyclohexyl group and the like. Specifically, it can be selected from the group consisting of a cyclopropylmethyl group, a cyclopentylmethyl group, a 2-cyclopentylethyl group, a 3-cyclopentylpropyl group, a cyclobutyl group, a cyclopentyl group and the like. Examples of the compound of the present invention represented by the aforementioned general formula (I) are, specifically, cyclopropylmethyl β-glucoside, cyclobutyl β-glucoside, cyclobutylmethyl β-glucoside, cyclopentyl β-glucoside, cyclopentylmethyl β-glucoside, 2-cyclopentylethyl β-glucoside, 3-cyclopentyl-1-propyl β-glucoside and the like.

The cycloalkyl β-glucoside of the present invention can be synthesized either by an organic synthetic process or enzymatic synthesis process. For the organic synthesis process, a method comprising a known reaction of glucose and alcohol in the presence of an acid catalyst can be used, and the compounds can be readily produced by one step through such a method (see Japanese Patent Unexamined Publication [KOKAI] No. 48-32846). As the aforementioned catalyst, hydrochloric acid, sulfuric acid, strongly acidic cation exchange resin and the like can be used. The cycloalkyl β-glucoside can be produced by adding the catalyst to a mixture of saccharide and alcohol, and stirring the mixture at a reaction temperature of 0–100° C. In addition to the above method, a method utilizing the known Koenigs-Knorr reaction to exclusively synthesize a β-linked compound (Yu Kagaku [oil Science], Vol. 43, No. 1, 31–38, (1994)) can also be used for the present invention.

As for the enzymatic synthesis process, the compound can readily be synthesized by utilizing the known transglucosylation reaction by β-glucosidase (see Japanese Patent Unexamined Publication No. 63-25859). Specifically, the β-glucoside can be produced by utilizing a cellulosic saccharide such as cellobiose, holocellulose, and xylan as a donor substrate, and an alcohol as an acceptor substrate, and allowing β-glucosidase to act on them.

As the cyclic alcohol used as a raw material in the aforementioned organic synthesis or the enzymatic synthesis, cyclopropanol, cyclobutanol, cyclobutylmethanol, cyclopentanol, cyclopentylmethanol, 2-cyclopropylethanol, 3-cyclopropyl-1-propanol and the like can be mentioned.

The obtained product containing β-glucoside can be further purified if required. As the method which can be used for the purification, for example, gel filtration chromatography, strongly acidic cation exchange resin chromatography, adsorption chromatography and the like can be mentioned. Specifically, the purification can be performed as follows. A reaction mixture of organic synthesis or enzymatic reaction is loaded on a column filled with a synthetic adsorption resin so that the cycloalkyl β-glucoside should be adsorbed on the resin, and the column is washed with water for removing un-adsorped materials. Then, the adsorbed cycloalkyl β-glucoside is eluted with 30 to 100% methanol to obtain concentrated cycloalkyl β-glucoside. The obtained concentrate can further be purified by gel filtration chromatography.

βGlucosidase Inhibitor

The β-glucosidase inhibitor of the present invention comprises as an active ingredient at least one of the β-glucoside represented by the aforementioned general formula (I). The β-glucoside represented by the aforementioned general formula (I), and the group R and the cyclic hydrocarbon group in the general formula (I) are similar to those explained above for the cycloalkyl β-glucoside of the present invention.

While the β-glucosidase inhibitor of the present invention can be used for both of β-glucosidases derived from plant and microorganism, it can preferably be used for β-glucosidase derived from plant.

Aromatic Substance Formation Inhibitor and Plant or Part thereof in which Formation of Aromatic Substance is Inhibited The aromatic substance formation inhibitor of the present invention comprises as an active ingredient at least one of the β-glucoside represented by the aforementioned general formula (I). The β-glucoside represented by the aforementioned general formula (I), and the group R and the cyclic hydrocarbon group in the general formula (I) are similar to those explained above for the cycloalkyl β-glucoside of the present invention.

The aromatic substance formation inhibitor of the present invention can be used for the inhibition of plant aromatic substance formation. As the plant of the present invention, therophytes, perennial herbaceous plants, and flowering trees such as gypsophila, lily, chrysanthemum, rose, jasmine, lavender, tulip, carnation, orchid, and sweet pea can be mentioned. However, it is not limited to these categories. The aromatic substance formation inhibitor of the present invention inhibits the formation of aromatic substance by inhibiting the aromatic substance formation in plant bodies. Therefore, the plant of which formation of the aromatic substance should be inhibited may be one in a state that the aromatic substance can be formed. For example, they may be cut flowers or those cultured in open, house, flowerpot and the like.

Since the aromatic substance formation inhibitor of the present invention exhibits high solubility in water and storage stability as an aqueous solution, it can be used as an aqueous solution, for example. Since the aromatic substance formation inhibitor of the present invention inhibits the activity of β-glucosidase in a plant body, the inhibitor must be introduced into the plant body in order to obtain the aromatic substance formation inhibition effect in the plant body by the inhibitor. To this end, for example, the following methods can be used.

When an aqueous solution is used for inhibiting the formation of the aromatic substance of plants, for example, in the case of cut flowers, cut ends of the cut flowers can be immersed in the aqueous solution of the aromatic substance formation inhibitor of the present invention, and thereby the aromatic substance formation inhibitor of the present invention can be absorbed through vessels of the cut flowers. This operation can be carried out easily, since special treatment is not required. Furthermore, such an aqueous solution as mentioned above can similarly be used in many scenes, for example, when flowers are temporarily immersed in water after the harvest by producers, when cut flowers are sold in shops such as flower shops in containers such as buckets, when cut flowers are arranged in vases at home, hospital, exhibition, etc. and the like. Further, such an aqueous solution can also be used for affusion or direct spraying on leaf surfaces so that the inhibitor should be absorbed in a plant, thereby inhibiting the formation of the aromatic substance of the plant. This method can be used for, for example, cut flowers and plants grown on open, in houses, flowerpots and the like. Specifically, an aqueous solution of the aromatic substance formation inhibitor of the present invention in a suitable amount can be affused into soil or sprinkled on leaf surfaces of plants.

Although concentration of the cycloalkyl β-glucoside used as an aromatic substance formation inhibitor of the present invention may vary depending on the kind of objective cut flowers or treatment time, when used as an aqueous solution, it is generally preferable to use it within a concentration range of about 0.01 to 10% by weight volum, more preferably about 0.1 to 3.0% by weight volum. The aromatic substance formation inhibitor of the present invention can function so long as the cycloalkyl β-glucoside functions as an active ingredient. Therefore, the aromatic substance formation inhibitor and plant or a part thereof of which formation of aromatic substance is to be inhibited may contain impurities, specifically, impurities introduced during the organic synthesis or enzymatic synthesis, so long as the plant is not adversely affected.

Furthermore, the aromatic substance formation inhibitor of the present invention can be used with a known cut flower life lengthening agent, for example, those comprising saccharide and germicide, surface active agent and the like, if required. Furthermore, the aromatic substance formation inhibitor of the present invention can also contain conventionally used nutrients such as nitrogen source, phosphoric acid, potassium source, sucrose, glucose, and vitamin C, trace amount nutrients such as iron, zinc, manganese, copper, and boron, B-nine, benzyladenine, brassinolide and the like.

The plant or part thereof in which the formation of the aromatic substance is inhibited by the aromatic substance formation inhibitor of the present invention means a plant or a part thereof in which the formation of the aromatic substance is inhibited by the aforementioned method utilizing the aromatic substance formation inhibitor of the present invention. The plant may be, for example, cut flowers or those cultured in open, house, flowerpot and the like. The part of plant may be, for example, a flower or a part containing flower, leaf or a part containing leaf, stalk or a part containing stalk and the like. As the kind of the aforementioned plant, for example, therophytes, perennial herbaceous plants, and flowering trees such as gypsophila, lily, chrysanthemum, rose, jasmine, lavender, tulip, carnation, orchid, and sweet pea can be mentioned. However, it is not limited to these categories.

Since formation of unpleasant aroma or aroma desired to be reduced is prevented in the plant or part thereof of the present invention, the emitted aromatic substance therefrom is reduced compared with that originally emitted from the corresponding plant or part thereof. Therefore, the plant or part thereof can be used for their applications without caring about their aroma. Specifically, when the aromatic substance formation of lily cut flowers is inhibited, they can be used for indoor decoration or the like without caring about their aroma, since their aroma said to be unpleasant is reduced.

Plant Life Lengthening Agent

The plant life lengthening agent of the present invention comprises as an active ingredient at least one of the β-glucoside represented by the aforementioned general formula (I). The β-glucoside represented by the aforementioned general formula (I), and the group R and the cyclic hydrocarbon group in the general formula (I) are similar to those explained above for the cycloalkyl β-glucoside of the present invention.

While the action mechanism of the plant life lengthening agent of the present invention is not clear, it gives to plant bodies life lengthening effect without causing phytotoxicity. As the plant of the present invention, therophytes, perennial herbaceous plants, and flowering trees such as gypsophila, lily, chrysanthemum, rose, jasmine, lavender, tulip, carnation, orchid, and sweet pea can be mentioned. However, it is not limited to these categories. The plant life lengthening agent of the present invention can be used for cut parts of the aforementioned plants, for example, cut flowers.

Since the plant life lengthening agent of the present invention is excellent in solubility in water and storage stability as an aqueous solution, it can be used as an aqueous solution, for example. When an aqueous solution is used for lengthening plant life, methods and amounts similar to those used for the aqueous solution of the aromatic substance formation inhibitor of the present invention for cut flowers can be used.

The present invention will be further explained with reference to the following examples hereinafter.

EXAMPLE 1

Organic Synthesis of Cycloalkyl β-glucoside

Anhydrous glucose (1.0 g, 5.6 mol), strongly acidic cation exchange resin Amberlyst 15E (ORGANO CORP., 1. 0 ml)

and cyclopentanol (2.0 ml) were mixed and stirred sufficiently, and the obtained mixture was incubated at 80 °C. The reaction mixture was sampled by collecting a 50 µl portion into a microtube at constant intervals. Each collected sample was added with 500 µl of 50% v/v methanol in purified water, and filtered through a 0.45 µm membrane filter, and 10 µl of the filtrate was subjected to HPLC using a gel filtration column to trace the saccharide composition. The aforementioned HPLC was performed by using a column Shodex Asahipak GS-220HQ (7.5 mm I.D.×500 mm), desalted water as eluate, and RI monitor as detector under the conditions of column temperature of 60° C. and flow rate of 0. 6 ml /min. After the reaction was performed for 24 hours, the obtained reaction mixture was cooled, and loaded on a column (2.5 cm I.D.×16 cm) filled with synthetic adsorptive resin HP-20 (Mitsubishi Chemical Co.), and washed with water. Then, the desired compound, cyclopentanol glycoside was eluted with 50% methanol, and concentrated. Further, the obtained concentrate was adjusted to 5% w/v concentration and pH 6.0, and added with 50 U of α-glucosidase from yeast at 40° C. to hydrolyze cycloalkyl α-glucoside contained as an impurity. After 24 hours, the reaction mixture was boiled for 5 minutes, removed unsloble materials by centrifugation, then concentrated the supernatant to 3 ml (40% w/v, 1.2 g as solid matter), and purified by gel filtration utilizing a column (5 cm, I.D.×95 cm) filled with Toyopearl HW-40S (Tosoh) and RI monitor as detector under the conditions of column temperature of 65° C. and flow rate of 5 ml/min to obtain 500 mg of cyclopentyl β-glycoside having a purity of 99% or more.

$^{13}$C Nuclear magnetic resonance spectrum of the obtained cyclopentyl β-glycoside was determined in heavy water utilizing tetramethylsilane as a standard. As a result, the peaks at 23.4, 38.0, 61.4, 70.0, 73.4, 75.2, 81.8, and 103.4 ppm were obtained. Further, $^1$H nuclear magnetic resonance spectrum was also determined. As a result, the anomeric proton was observed at 4.48 ppm as a doublet peak, and the coupling constant was 7.91 Hz. From these results, it could be confirmed that the obtained glycoside was cyclopentyl β-glucoside.

Furthermore, the same reaction and HPLC analysis as mentioned above were repeated by using cyclobutanol, cyclopentylmethanol, 2-cyclopentylethanol, and 3-cyclopentyl-l-propanol instead of cyclopentanol. As a result, the formation of β-glucoside could be confirmed for each case.

EXAMPLE 2

Enzymatic Synthesis of Cycloalkyl β-glucoside

Cellobiose (10 g, final concentration; 25% w/w), 100 mM sodium acetate buffer (pH 5.0, 2 ml), pure water (30.4 ml), and cyclopentylmethanol (5 ml) were mixed sufficiently, added with 5 U of enzyme preparation containing β-glucosidase derived from *Trichoderma viride* (Cellulase, SIGMA), and left stand for reaction at 45° C. The reaction mixture was sampled by collecting a 50 µl portion into a microtube. Each collected sample was boiled for 5 minutes, added with 500 µl of purified water, and filtered through a 0.45 µm membrane filter, and 10 µl of the filtrate was subjected to the same HPLC as in Example 1 to trace the saccharide composition. After the reaction by β-glucosidase for 48 hours, the obtained reaction mixture was boiled for 10 minutes to inactivate the enzyme. The reaction mixture was loaded on a column (2.5 cm I.D.×16 cm) filled with synthetic adsorptive resin HP-20 (Mitsubishi Chemical Co.), and washed with water, and cyclopentylmethanol glycoside was eluted with 50% methanol, and concentrated. The reaction mixture concentrated to 3 ml (40% w/v, 1.2 g as solid matter) was purified by gel filtration utilizing a column (5 cm, I.D.×95 cm) filled with Toyopearl HW-40S (Tosoh) and RI monitor as detector under the conditions of column temperature of 65° C. and flow rate of 5 ml/min to obtain 500 mg of cyclopentylmethanol glycoside having a purity of 99% or more.

$^{13}$C Nuclear magnetic resonance spectrum of the obtained cyclopentylmethanol glycoside was determined in heavy water utilizing tetramethylsilane as a standard. As a result, the peaks at 27.8, 31.8, 31.9, 41.5, 63.5, 72.5, 76.0, 78.0, 78.7, 78.8, and 105.2 ppm were obtained. Further, $^1$H nuclear magnetic resonance spectrum was also determined. As a result, the anomeric proton was observed at 4.45 ppm as a doublet peak, and the coupling constant was 7.92 Hz. From these results, it could be confirmed that the obtained cyclopentylmethanol glycoside was cyclopentylmethyl-β-glucoside.

Furthermore, the same reaction and HPLC analysis as mentioned above were repeated by using cyclopropylmethanol, cyclobutanol, and cyclopentylethanol instead of cyclopentylmethanol. As a result, the formation of β-glucoside could be confirmed for each case.

EXAMPLE 3

β-Glucosidase Inhibition Test

β-Glucosidase inhibition test was performed as follows. 10 mM p-nitrophenyl-β-glucoside (100 µl, abbreviated as pNP-β-Glc hereinafter), 1 M sodium acetate buffer (pH 5.0, 50 µl), pure water, and 100 mM inhibitor (10 µl) were taken into a short test tube so that the mixture should have a total volume of 800 µl, and preincubated at 40° C. for 5 minutes. After the incubation, the obtained mixture was added with 50 µl of enzyme solution diluted to a suitable concentration, and allowed to react at 40° C. After 10 minutes, the enzyme was inactivated by adding 500 µl of 1 M sodium carbonate to the obtained reaction mixture, and the absorbance at 405 nm was measured and used for calculation of the amount of free p-nitrophenol. As the inhibitor, cyclopropylmethyl-β-glucoside (CPAM-β-Glc), cyclopentyl-β-glucoside (CPE-β-Glc), and cyclopentylmethyl-β-glucoside (CPEM-β-Glc) all prepared by the methods of Examples 1 and 2 were used. As the β-glucosidase, chromatographically purified preparations derived from *Aspergillus niger*, *Trichoderma viride*, and Almond (all from SIGMA) were used.

TABLE 1

Effect of cycloalkyl glucoside (1 mM) on pNP-β-glucosidase activity

| Enzyme | Inhibitor | Activity ratio |
| --- | --- | --- |
| 1) *A. niger* | No inhibitor | 1.00 |
| | CPMA-β-Glc | 0.94 |
| | CPE-β-Glc | 0.92 |
| | CPEM-β-Glc | 0.99 |
| 2) *T. viride* | No inhibitor | 1.00 |
| | CPAM-β-Glc | 1.01 |
| | CPE-β-Glc | 1.06 |
| | CPEM-β-Glc | 1.05 |
| 3) Almond | No inhibitor | 1.00 |
| | CPAM-β-Glc | 0.86 |
| | CPE-β-Glc | 0.90 |
| | CPEM-β-Glc | 0.27 |

As shown in the above results, under the aforementioned experimental condition (inhibitor concentration of 1.25 mM), CPEM-β-Glc strongly inhibited the β-glucosidase derived from almond, but showed relatively weak inhibition for that derived from *A. niger*, and no inhibition for that derived from *T. viride*. Therefore, the measurement was further performed under the same conditions as those mentioned above with a concentration of CPEM-β-Glc varying from 0 to 5 mM. As a result, the 50% inhibition concentration of CPEM-β-Glc for the β-glucosidase derived from almond was found to be 0.17 mM, and 50% inhibition concentrations for β-glucosidases derived from *A. niger* and *T. viride* were found to be 12.61 and 11.54 mM, respectively. Thus, it was demonstrated that, although CPEM-β-Glc showed difference in the effective concentration (50% inhibition concentration for β-glucosidase derived from almond was about 70 times higher than 50% inhibition concentrations for β-glucosidases derived from *A. niger* and *T. viride*), it inhibited all of the β-glucosidases.

EXAMPLE 4
Inhibition Test for Rose Crude Enzyme

Only petals (about 70 g) were collected from about ten marketed roses (variety; Rosa gybrida CV. Wendy), added with acetone (500 ml) cooled to −20° C., and pulverized by a homogenizer while cooled with dry ice. The obtained pulverized mixture was filtered through a Buchner funnel put with a No. 2 filter paper sheet, and sufficiently washed with acetone at −20° C. The obtained filtrate was dried in a desiccator under reduced pressure (room temperature, 3 hours) to obtain 6 g of crude enzyme powder. This powder was added to 100 mM sodium phosphate buffer (pH 7.0, 120 ml) and stirred at 4° C. for 3 hours, and the insoluble matter was removed by centrifugation. The filtrate was subjected to ultrafiltration utilizing an ultrafiltration membrane PM-10 (Amicon) to finally afford 15 ml of crude enzyme solution.

In the same manner as in Example 3, the inhibition activity of the CPEM-β-Glc obtained in Example 2 for the pNP-β-Glc activity of the above crude enzyme solution was measured. The measurement was performed by varying the concentration of the added CPEM-β-Glc from 0 to 5 mM. As a result, the inhibition activity was about 50% at 3 mM, about 70% at 4 mM, and about 90% at 5 mM.

EXAMPLE 5
Aromatic Substance Formation Inhibition Effect in Cut Flowers

A 0.13% (w/v, 5 mM) aqueous solution of the CPEM-β-Glc obtained in Example 2 was prepared. The obtained aqueous solution (300 ml) was introduced into an Erlenmeyer flask, and lily, chrysanthemum, and gypsophila were put into it one for each. On the other hand, as control, the flowers were similarly put into water without the CPEM-β-Glc. After 1, 2 and 4 days, organoleptic test was performed by ten expert panelists as for the aroma emitted from these cut flowers. As a result, after one day, all of the expert panelists judged that the aroma was distinctly reduced when the CPEM-β-Glc was added as for all of lily, chrysanthemum, and gypsophila. No difference in freshness of the cut flowers was observed between the cases where the CPEM-β-Glc was added or not added.

EXAMPLE 6
Life Lengthening Effect for Cut Flowers

A 0.13% (w/v, 5 mM) aqueous solution of the CPEM-β-Glc obtained in Example 2 was prepared. The obtained aqueous solution (50 ml) was introduced into an Erlenmeyer flask, and a rose (variety; Rosa gybrida CV. Dukat) in a budding state was put into it. On the other hand, as control, the flower was similarly put into water not added with the CPEM-β-Glc. The flowers were left at room temperature, and droop of the flowers was observed. The flower did not droop by the 7th day when CPEM-β-Glc was added, whereas the flower drooped on the 5th day when CPEM-β-Glc was not added.

Unlike β-glucosides containing a nitrogen atom, of which industrial production is difficult, the compounds of the present invention represented by the general formula (I) have a relatively simple structure, and therefore they can be produced by an organic synthesis process or enzymatic synthesis process suitable for the industrial production. Therefore, it has become possible to industrially produce and provide β-glucosides, of which industrial production has hitherto been difficult. By utilizing the β-glucosidase inhibition activity of the compounds represented by the general formula (I) of the present invention, for example, it has become possible to provide plant aromatic substance formation inhibitors containing the foregoing compounds as an active ingredient and capable of alleviating unpleasant fragrance or unnecessarily strong fragrance of cut flowers and the like, and plant bodies whose aromatic substance formation is inhibited by the aromatic substance formation inhibitors. Because the cycloalkyl β-glucosides of the present invention are a non-odorous substance, an inhibition effect for the aromatic substance formation is not degraded by the odor of the β-glucosides themselves. Further, because the aromatic substance formation inhibitors of the present invention do not show phytotoxicity against plants, they can be used without caution. Furthermore, because the compounds of the present invention also have plant life lengthening effect, they can be readily used as a plant life lengthening agent without showing phytotoxicity.

What is claimed is:

1. A compound represented by the following general formula I:

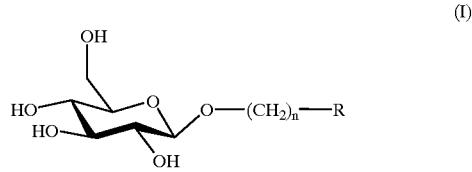

wherein R represents a cyclic hydrocarbon group selected from the group consisting of a cyclopropylmethyl group, a cyclopentylmethyl group, a 2-cyclopentylethyl group, a 3-cyclopentylpropyl group, cyclobutyl group, and a cyclopentyl group, and n represents 0 (zero) or an integer not less than 1.

2. The compound of claim 1 wherein the n is not greater than 3.

3. An aromatic substance formation inhibiting composition consisting essentially of at least one compound of claim 1 as an active ingredient.

4. A plant life lengthening composition consisting essentially of at least one compound of claim 1 as an active ingredient.

5. A compound according to claim 1, wherein said compound is cyclopropylmethyl β-glucoside, cyclobutyl β-glucoside, cyclobutylmethyl β-glucoside, cyclopentyl β-glucoside, cyclopentylmethyl β-glucoside, 2-cyclopentylethyl β-glucoside, or 3-cyclopentyl-1-propyl β-glucoside.

* * * * *

UNITED STATES PATENT AND TRADEMARK OFFICE
CERTIFICATE OF CORRECTION

PATENT NO. : 6,339,146 B1
DATED : January 15, 2002
INVENTOR(S) : Koichi Ogawa

It is certified that error appears in the above-identified patent and that said Letters Patent is hereby corrected as shown below:

<u>Title page,</u>
Item [*], Notice, delete "This patent issued on a continued prosecution application filed under 37 C.F.R. 1.53(d), and is subject to the twenty year patent term provisions of 35 U.S.C. 154(a)(2)."

Signed and Sealed this

Ninth Day of July, 2002

Attest:

Attesting Officer

JAMES E. ROGAN
*Director of the United States Patent and Trademark Office*